United States Patent
Jiao et al.

(10) Patent No.: US 11,999,671 B2
(45) Date of Patent: Jun. 4, 2024

(54) METHOD FOR PREPARING LIGHT OLEFIN THROUGH CATALYTIC SYNGAS WITH HIGH SELECTIVITY BY HETEROATOM-DOPED ZEOLITE

(71) Applicant: DALIAN INSTITUTE OF CHEMICAL PHYSICS, CHINESE ACADEMY OF SCIENCES, Dalian (CN)

(72) Inventors: Feng Jiao, Dalian (CN); Gen Li, Dalian (CN); Xiulian Pan, Dalian (CN); Xinhe Bao, Dalian (CN)

(73) Assignee: DALIAN INSTITUTE OF CHEMICAL PHYSICS, CAS, Dalian (CN)

( * ) Notice: Subject to any disclaimer, the term of this patent is extended or adjusted under 35 U.S.C. 154(b) by 552 days.

(21) Appl. No.: 17/286,903

(22) PCT Filed: Dec. 10, 2019

(86) PCT No.: PCT/CN2019/124234
§ 371 (c)(1),
(2) Date: Apr. 20, 2021

(87) PCT Pub. No.: WO2020/125487
PCT Pub. Date: Jun. 25, 2020

(65) Prior Publication Data
US 2021/0347711 A1   Nov. 11, 2021

(30) Foreign Application Priority Data

Dec. 21, 2018 (CN) .......................... 201811575056.4
Dec. 21, 2018 (CN) .......................... 201811575060.0

(51) Int. Cl.
C07C 1/04 (2006.01)
B01J 8/02 (2006.01)
(Continued)

(52) U.S. Cl.
CPC ................. *C07C 1/044* (2013.01); *B01J 8/02* (2013.01); *B01J 8/24* (2013.01); *B01J 19/14* (2013.01); *B01J 21/04* (2013.01); *B01J 21/066* (2013.01); *B01J 23/002* (2013.01); *B01J 23/06* (2013.01); *B01J 23/08* (2013.01); *B01J 23/10* (2013.01); *B01J 23/18* (2013.01); *B01J 23/26* (2013.01); *B01J 23/34* (2013.01); *B01J 23/745* (2013.01); *B01J 23/75* (2013.01); *B01J 29/85* (2013.01); *B01J 35/19* (2024.01); *B01J 35/613* (2024.01); *B01J 35/615* (2024.01); *B01J 37/0036* (2013.01); *B01J 37/009* (2013.01); *B01J 37/0201* (2013.01); *B01J 37/031* (2013.01); *B01J 37/04* (2013.01); *B01J 37/06* (2013.01); *B01J 37/082* (2013.01); *B01J 37/10* (2013.01); *B01J 37/18* (2013.01); *C07C 1/0435* (2013.01); *B01J 2229/18* (2013.01); *C07C 2521/04* (2013.01); *C07C 2521/06* (2013.01); *C07C 2523/06* (2013.01); *C07C 2523/08* (2013.01); *C07C 2523/10* (2013.01); *C07C 2523/18* (2013.01); *C07C 2523/26* (2013.01); *C07C 2523/34* (2013.01); *C07C 2523/745* (2013.01); *C07C 2523/75* (2013.01)

(58) Field of Classification Search
CPC ....... B01J 8/02; B01J 8/24; B01J 19/14; B01J 21/04; B01J 21/066; B01J 23/002; B01J 23/06; B01J 23/08; B01J 23/10; B01J 23/18; B01J 23/26; B01J 23/34; B01J 23/745; B01J 23/75; B01J 29/85; B01J 35/613; C07C 1/044; C07C 1/043
See application file for complete search history.

(56) References Cited

U.S. PATENT DOCUMENTS

2019/0275505 A1   9/2019   Bao et al.
2021/0002184 A1   1/2021   Pan et al.

FOREIGN PATENT DOCUMENTS

CN   1083415 A    9/1994
CN   1242845 C2   2/2006
(Continued)

OTHER PUBLICATIONS

Written Opinion dated Mar. 9, 2020 for related International Patent Application No. PCT/CN2019/124234 issued by the international searching authority.
(Continued)

Primary Examiner — Jafar F Parsa
(74) Attorney, Agent, or Firm — MagStone Law, LLP; Enshan Hong

(57) ABSTRACT

A composite catalyst containing heteroatom-doped zeolite for preparing light olefin using direct conversion of syngas is formed by compounding component I and component II in a mechanical mixing mode. The active ingredient of component I is a metal oxide, and the component II is a heteroatom-doped zeolite. The zeolite topology is CHA or AEI, and the skeleton atoms include Al—P—O or Si—Al—P—O; the heteroatoms is at least one of divalent metal Mg, Ca, Cr, Mn, Fe, Co, Ni, Cu, Zn, Sr, Zr, Mo, Cd, Ba and Ce, trivalent metal Ti and Ga, and tetravalent metal Ge. A weight ratio of the active ingredient in the component I to the component II is 0.1-20. The reaction process has high light olefin selectivity; the sum selectivity of the light olefin including ethylene, propylene and butylene can reach 50-90%, while the selectivity of a methane side product is less than 7%.

15 Claims, No Drawings

(51) Int. Cl.
*B01J 8/24* (2006.01)
*B01J 19/14* (2006.01)
*B01J 21/04* (2006.01)
*B01J 21/06* (2006.01)
*B01J 23/00* (2006.01)
*B01J 23/06* (2006.01)
*B01J 23/08* (2006.01)
*B01J 23/10* (2006.01)
*B01J 23/18* (2006.01)
*B01J 23/26* (2006.01)
*B01J 23/34* (2006.01)
*B01J 23/745* (2006.01)
*B01J 23/75* (2006.01)
*B01J 29/85* (2006.01)
*B01J 35/00* (2006.01)
*B01J 35/61* (2024.01)
*B01J 37/00* (2006.01)
*B01J 37/02* (2006.01)
*B01J 37/03* (2006.01)
*B01J 37/04* (2006.01)
*B01J 37/06* (2006.01)
*B01J 37/08* (2006.01)
*B01J 37/10* (2006.01)
*B01J 37/18* (2006.01)

(56) References Cited

FOREIGN PATENT DOCUMENTS

| | | |
|---|---|---|
| CN | 107661773 A | 2/2018 |
| CN | 107661774 A | 2/2018 |
| CN | 108144643 A | 6/2018 |
| CN | 108568313 A | 9/2018 |
| CN | 108970600 A | 12/2018 |
| WO | 2009051353 A2 | 4/2009 |
| WO | WO-2018103603 A1 * | 6/2018 ............ B01J 23/005 |

OTHER PUBLICATIONS

International Search Report dated Mar. 9, 2020 for related International Patent Application No. PCT/CN2019/124234 issued by the international searching authority.

Jiao et al., "Selective conversion of syngas to light olefins", Science, 351 (2016) 1065-1068.

Hirsa M. Torres Galvis et al., "Supported Iron Nanoparticles as Catalysts for Sustainable Production of Lower Olefins", Science 335 (6070), 835-838 (Feb. 17m, 2012).

* cited by examiner

METHOD FOR PREPARING LIGHT OLEFIN THROUGH CATALYTIC SYNGAS WITH HIGH SELECTIVITY BY HETEROATOM-DOPED ZEOLITE

RELATED APPLICATIONS

This is a U.S. national stage of international application No. PCT/CN2019/124234 filed on Dec. 10, 2019, which claims priority from China Patent Application Nos. 201811575060.0 filed on Dec. 21, 2018 and 201811575056.4 filed on Dec. 21, 2018, the entire content of which is incorporated herein as reference.

TECHNICAL FIELD

The present invention belongs to field of preparation of light olefin through syngas, and particularly relates to a method for preparing light olefin through catalytic syngas with high selectivity by a heteroatom-doped zeolite.

BACKGROUND

Light olefin refers to alkene with the number of carbon atoms less than or equal to 4. Light olefin represented by ethylene and propylene are very important basic organic chemical raw materials. With the fast growth of economy in China, the market of the light olefin is in short supply for a long time. At present, the light olefin is produced mainly through a petrochemical route of cracking of light hydrocarbon (ethane, naphtha and light diesel fuel). Due to the increasing shortage of global petroleum resources and the long-term high-price operation of crude oil, the development of the light olefin industry relying only on a tubular cracking furnace technology that uses petroleum light hydrocarbon as raw material will encounter more and more difficulties in raw material. The production technology and the raw material of the light olefin must be diversified. A technology for preparing alkene using syngas can widen the source of the raw material, and will provide an alternative solution for a steam cracking technology based on high-cost raw material such as naphtha by production of syngas using crude oil, natural gas, coal and renewable material as raw material. One-step direct preparation of the light olefin using the syngas is a process of directly preparing the light olefin with the number of carbon atoms less than or equal to 4 through Fischer-Tropsch synthesis reaction of carbon monoxide and hydrogen under the action of the catalyst. This process simplifies the process flow and greatly reduces the investment unlike an indirect method that further prepares the alkene from the syngas and the methanol or dimethyl ether.

Direct preparation of the light olefin using the syngas through Fischer-Tropsch synthesis has become one of research hotspots in development of catalyst for Fischer-Tropsch synthesis. In patent CN1083415A disclosed by Dalian Institute of Chemical Physics, Chinese Academy of Sciences, high activity (CO conversion rate: 90%) and selectivity (light olefin selectivity: 66%) can be obtained under reaction pressure of 1.0 to 5.0 MPa and reaction temperature of 300 to 400° C. in preparation of the light olefin from the syngas under the auxiliary of alkali K or Cs ion by using an iron-manganese catalyst system carried by IIA alkali metal oxide such as MgO or silica rich zeolite (or phosphorous-aluminum zeolite). In patent ZL03109585.2 declared by Beijing University of Chemical Technology, Fe/activated carbon catalyst with manganese, copper, zinc, silicon and potassium as auxiliaries is prepared by a vacuum impregnation method for the reaction of preparation of the light olefin from the syngas. Under the condition of no feedstock gas circulation, the CO conversion rate is 96%, and the selectivity of the light olefin in hydrocarbons is 68%. Recently, professor de Jong's team at Utrecht university in Netherlands made good progress by using Fe catalyst modified by Fe, Na, S and other auxiliaries supported by SiC, carbon nanofiber and other inert carriers, obtained 61% of selectivity of lower alkene. However, the selectivity is reduced when the conversion rate is increased. In direct preparation of the alkene using the syngas, because raw material of CO and $H_2$ are gaseous and the ethylene in a target product has a low boiling point, cryogenic separation is needed generally. If the alkene containing three carbon atoms or four carbon atoms is obtained with high selectivity, i.e., $C_3$-$C_4$ alkene product of propylene and butylene, cryogenic separation is not needed, thereby greatly reducing energy consumption and cost for separation and bringing great application value. In the above report, the catalyst uses metal iron or iron carbide as the active component. The reaction follows the chain growth mechanism of metal surfaces. The selectivity of the product lower alkene is low, while the selectivity of $C_3$-$C_4$ alkene is lower.

Recently, a composite bifunctional catalyst of $ZnCr_2O_4$ oxide and hierarchical pore SAPO-34 zeolite has reported by Dalian Institute of Chemical Physics, Chinese Academy of Sciences (Jiao et al., Science 351 (2016) 1065-1068), which has realized 80% of selectivity of the lower alkene when the conversion rate of CO is 17%, wherein the selectivity of the lower alkane is 14% and the alkene/alkane ratio is 5.7. When the conversion rate is increased to 35%, the alkene selectivity is 69%, alkane selectivity is 20%, alkene/alkane ratio is decreased to 3.5 and propylene and butylene selectivity is 40-50%.

SUMMARY OF THE INVENTION

In view of the above problems, the present invention provides a catalyst and a catalyst and method for preparing light olefin using direct conversion of syngas.

The Technical Solution of the Present Invention is:

In one aspect, the present invention provides a catalyst which comprises component I and component II; the component I and the component II are prepared separately and then mixed. The active ingredient of the component I is a metal oxide, and the component II is a heteroatom-doped zeolite.

The metal oxide is one or more than one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$; the value range of x is 0.7-3.7; the value range of a is 0-1; and the value range of a+b is 0-1.

The zeolite is a zeolite with CHA or AEI topology; skeleton atoms comprise Al—P—O or Si—Al—P—O; heteroatoms are one or more than one of divalent metal Mg, Ca, Cr, Mn, Fe, Co, Ni, Cu, Zn, Sr, Zr, Mo, Cd, Ba and Ce, trivalent metal Ti and Ga, and tetravalent metal Ge; the heteroatom-doped zeolite means that the heteroatoms are doped in a zeolite skeleton to replace Al or P or Si in the zeolite skeleton. The bivalent metal and the trivalent metal generally replace Al position in the skeleton, and metal with four or more valence replaces P or Si position.

Based on the above technical solution, preferably, the specific surface area of $MnO_x$, $ZnO_x$, $CeO_x$, $GaO_x$, $BiO_x$ and $InO_x$ is 1-100 m²/g; and a preferred specific surface area is 50-100 m²/g.

The specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CO_aAl_{(1-a)}O_x$, $Fe_aAl_{(1-a)}O_x$, $In_aAl_bMn_{(1-a-b)}O_x$ and $In_aGa_bMn_{(1-a-b)}O_x$ is 5-150 m²/g; and a preferred specific surface area is 50-150 m²/g.

Based on the above technical solution, preferably, a ratio of the sum of the molar weight of the heteroatoms in the heteroatom-doped zeolite to the molar weight of P is 0.001-0.6; and a ratio of the molar weight of Si atom to P is 0.01-0.6.

Based on the above technical solution, preferably, a weight ratio of the active ingredient in the component I to the component II is 0.1-20, and preferably 0.3-5.

Based on the above technical solution, preferably, a dispersant is added to the component I, and the metal oxide is dispersed in the dispersant; the dispersant is one or more than one of $Al_2O_3$, $SiO_2$, $Cr_2O_3$, $ZrO_2$, $TiO_2$, $Ga_2O_3$, activated carbon, graphene and carbon nanotube; and in the component I, the content of the dispersant is 0.05-90 wt %, and the balance is the metal oxide.

Based on the above technical solution, preferably, the heteroatom-doped zeolite is prepared by an in-situ hydrothermal growth method or a post-treatment method; the in-situ hydrothermal growth method comprises the following steps:

(1) preparation of a sol precursor:
Al—P—O skeleton: dissolving a certain proportion of aluminum source and phosphorus source in water; stirring evenly; then adding a heteroatom-containing precursor and a template agent into the solution; and stirring for 0.5-12 h;
Si—Al—P—O skeleton: dissolving a certain proportion of aluminum source, phosphorus source and silicon source in water; stirring evenly; then adding the heteroatom-containing precursor and the template agent; and stirring for 0.5-12 h;
(2) hydrothermal crystallization: crystallizing the sol precursor obtained in step (1) at 160-200° C. for 4-7 days;
(3) separation and washing: centrifuging and washing the product after the crystallization reaction;
(4) drying and roasting: roasting the product of step (3) at 550-600° C. for 3-6 h, wherein a ratio of the heteroatoms in the heteroatom precursor to the phosphorus source is 0-0.6.

The post-treatment method is:
Al—P—O skeleton: configuring the solution of the heteroatom precursor; impregnating AlPO-18 or AlPO-34 zeolite into the solution of the precursor; drying the solution; finally roasting the solution at 550-600° C. for 3-6 h; obtaining the heteroatom precursor by the impregnation method and other loads; and embedding the heteroatoms into the skeleton by roasting;
Si—Al—P—O skeleton: configuring the solution of the heteroatom precursor; impregnating SAPO-18 or SAPO-34 zeolite into the solution of the precursor; drying the solution; and finally roasting the solution at 550-600° C. for 3-6 h.

The AlPO-18 or AlPO-34, SAPO-18 or SAPO-34 may be commercially available samples or the samples synthesized by the methods reported in the literature.

The heteroatom-doped zeolite obtained by the above two methods is obviously different from the ion exchange zeolite in that it is difficult to dope the heteroatoms through ion exchange because the skeleton of the AEI zeolite having Al, P and O as the skeleton is electrically neutral and O has no exchangeable H atom. H on Si—OH—Al is generally replaced by heteroatoms of the zeolite having Si—Al—P—O as the skeleton after ion exchange, which is located outside the zeolite skeleton. The heteroatoms of the zeolite obtained by ion exchange are generally located outside the zeolite skeleton, regardless of the skeleton of Al—P—O or Si—Al—P—O. The heteroatoms of the heteroatom-doped zeolite obtained by the present invention are embedded into the zeolite skeleton, and the structure and reaction performance of the catalyst are obviously different from those of the ion exchange sample.

Based on the above technical solution, preferably, the aluminum source comprises, but not limited to, boehmite, aluminum hydroxide, aluminum nitrate, aluminum sulfate or aluminum isopropoxide; the phosphorus source comprises, but not limited to, phosphoric acid; the silicon source comprises, but not limited to, silica sol, TEOS, white carbon black, quartz sand and silicate; the heteroatom precursor comprises, but not limited to, metal nitrate, sulfate, acetate, halide or oxide of a corresponding metal atom; the template agent is triethylamine (TEA), diisopropylethylamine (DIPEA) and the like.

In another aspect, the present invention provides a method for preparing light olefin through catalytic syngas with high selectivity, which uses the syngas as reaction raw material to conduct a conversion reaction on a fixed bed or a moving bed to prepare light olefin. The catalyst adopted in the method is the above catalyst.

Based on the above technical solution, preferably, the pressure of the syngas is 0.5-10 MPa, preferably 1-8 MPa, and more preferably 2-8 MPa; reaction temperature is 300-600° C., and preferably 370-450° C.; space velocity is 300-10000 h⁻¹, preferably 500-9000 h⁻¹, and more preferably 1000-6000 h⁻¹; the syngas is mixed gas of $H_2/CO$, and a molar ratio of $H_2/CO$ is 0.2-3.5, and preferably 0.3-2.5; the syngas may also contain $CO_2$, and a volume concentration of $CO_2$ in the syngas is 0.1-50%.

Based on the above technical solution, preferably, $C_{2-4}$ olefin is prepared using one-step direct conversion of syngas by the method; the selectivity for $C_{2-4}$ olefin is 50-90%; and the selectivity for a methane side product is lower than 7%.

Beneficial Effects

Different from the traditional technology for preparing the light olefin through methanol (MTO for short), this technology realizes preparation of the light olefin through one-step direct conversion of syngas.

The preparation process of the composite catalyst of the present invention is simple and has mild conditions. The heteroatoms are embedded into the zeolite skeleton of CHA or AEI structure, so that the reaction activity and product selectivity are effectively improved. The selectivity for the light olefin is improved while the reaction conversion rate is increased. The reaction conversion rate can be up to 10%-55%; the selectivity for propylene and butene products is increased, and can be up to 40-75%; and the selectivity for $C_{2-4}$ light olefin can be up to 50-90%. The products are separated without deep cooling, thereby greatly reducing separation energy consumption and cost. Meanwhile, the selectivity for a methane side product is low (<7%), and the catalyst has long service life which is greater than 700 hours. The present invention has excellent application prospect.

DETAILED DESCRIPTION OF PREFERRED EMBODIMENTS

The present invention is further illustrated below through embodiments, but the scope of claims of the present invention is not limited by the embodiments. Meanwhile, the embodiments only give some conditions for achieving the purpose, but it doesn't mean that the conditions must be satisfied to achieve the purpose.

The specific surface area of the sample can be tested through a physical adsorption method of nitrogen or argon.

The metal oxide in the present invention can be obtained by purchasing a commercially available metal oxide with a high specific surface area, or obtained by the following methods:

I. Preparation of Component I of Catalyst (I) Synthesizing ZnO Material with High Specific Surface Area Through a Precipitation Method:

(1) 3 parts of 0.446 g (1.5 mmol) of $Zn(NO_3)_2 \cdot 6H_2O$ were respectively weighed into three containers; 0.300 g (7.5 mmol), 0.480 g (12 mmol) and 0.720 g (18 mmol) of NaOH were respectively weighed and successively added to the above three containers; 30 ml of deionized water was weighed and added to the three containers; the mixture was stirred for more than 0.5 h at 70° C. to uniformly mix the solution; and the solution was naturally cooled to room temperature. Reaction liquid was centrifugally separated to collect the centrifugally separated precipitate; and the precipitate was washed with deionized water twice to obtain ZnO metal oxide precursor.

(2) Roasting: after drying the obtained product in the air, the product was roasted in an atmosphere to obtain ZnO material with high specific surface area. The atmosphere is inert gas, reducing gas or oxidizing gas. The inert gas is one or more than one of $N_2$, He and Ar. The reducing gas is one or two of $H_2$ and CO, and the reducing gas may also contain the inert gas. The oxidizing gas is one or more than one of $O_2$, $O_3$ and $NO_2$, and the oxidizing gas may also contain the inert gas. Roasting temperature is 300-700° C., and time is 0.5 h-12 h.

The purpose of roasting is to decompose the precipitated metal oxide precursor into oxide nanoparticles with high specific surface area at high temperature, and clean the adsorbed species on the surface of the oxide generated by decomposition through the high temperature roasting treatment.

Specific samples and preparation conditions thereof are shown in Table 1 below. As a reference example, ZnO #4 in the table is a commercially available ZnO single crystal with low specific surface area.

TABLE 1

Preparation of ZnO Material and Parameter Performance

| Zinc Oxide Sample Number | Roasting Time/h | Roasting Temperature/° C. | Roasting Atmosphere | Specific Surface Area $m^2/g$ |
|---|---|---|---|---|
| ZnO#1 | 5 | 500 | Ar | 71 |
| ZnO#2 | 2 | 320 | 5%$H_2$/$N_2$ | 47 |
| ZnO#3 | 3 | 550 | Air | 15 |
| ZnO#4 | — | — | — | <1 |

(II) Synthesizing MnO Material with High Specific Surface Area Through a Coprecipitation Method:

The preparation process is the same as that of the above ZnO #2. The difference is that, the precursor of Zn is changed for the corresponding precursor of Mn, which may be one of manganous nitrate, manganese chloride and manganese acetate, and is manganous nitrate herein. The corresponding product is defined as MnO. The specific surface area is 23 $m^2/g$.

(III) Synthesizing $CeO_2$ Material with High Specific Surface Area Through the Coprecipitation Method:

The preparation process is the same as that of the above ZnO #2. The difference is that, the precursor of Zn is changed for the corresponding precursor of Ce, which may be one of cerium nitrate, cerium chloride and cereous acetate, and is cerium nitrate herein. The corresponding product is defined as $CeO_2$. The specific surface area is 92 $m^2/g$.

(IV) Synthesizing $Ga_2O_3$ Material with High Specific Surface Area Through a Coprecipitation Method:

The preparation process is the same as that of the above ZnO #2. The difference is that, the precursor of Zn is changed for the corresponding precursor of Ga, which may be one of gallium nitrate, gallium chloride and gallium acetate, and is gallium nitrate herein. The corresponding product is defined as $Ga_2O_3$. The specific surface area is 55 $m^2/g$.

(V) Synthesizing $Bi_2O_3$ Material with High Specific Surface Area Through a Coprecipitation Method:

The preparation process is the same as that of the above ZnO #2. The difference is that, the precursor of Zn is changed for the corresponding precursor of Bi, which may be one of bismuth nitrate, bismuth chloride and bismuth acetate, and is bismuth nitrate herein. The corresponding product is defined as $Bi_2O_3$. The specific surface area is 87 $m^2/g$.

(VI) Synthesizing $In_2O_3$ Material with High Specific Surface Area Through a Coprecipitation Method:

The preparation process is the same as that of the above ZnO #2. The difference is that, the precursor of Zn is changed for the corresponding precursor of In, which may be one of indium nitrate, indium chloride and indium acetate, and is indium nitrate herein. The corresponding product is defined as $In_2O_3$. The specific surface area is 52 $m^2/g$.

(VII) Synthesizing $Mn_aCr_{(1-a)}O_x$, $Mn_aAl_{(1-a)}O_x$, $Mn_aZr_{(1-a)}O_x$, $Mn_aIn_{(1-a)}O_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CO_aAl_{(1-a)}O_x$, $Fe_aAl_{(1-a)}O_x$, $In_aAl_bMn_{(1-a-b)}O_x$ and $In_aGa_bMn_{(1-a-b)}O_x$ with High Specific Surface Area Through a Precipitation Method:

Zinc nitrate, aluminum nitrate, chromic nitrate, manganese nitrate, zirconium nitrate, indium nitrate, cobalt nitrate and ferric nitrate were adopted as precursors, and mixed at room temperature in water (wherein for ammonium carbonate as a precipitant, a feeding ratio is excessive or the ratio of ammonium ions to metal ions is preferably 1:1). The above mixed solution was aged, and then taken out for washing, filtering and drying; and the obtained solid was roasted under an air atmosphere to obtain a metal oxide with high specific surface area. Specific samples and preparation conditions thereof are shown in Table 2 below.

TABLE 2

Preparation of Metal Oxide with High Specific Surface Area and Performance Parameters

| Metal Oxide | Feeding Ratio of Metal Elements and Final Molar Concentration of One Metal in Water, mmol/L | Aging Temperature °C. | Aging Time h | Roasting Temperature °C. | Roasting Time h | Specific Surface Area $m^2/g$ |
|---|---|---|---|---|---|---|
| $ZnCr_2O_4$ | ZnCr = 1:2, Zn is 50 mM | 120 | 24 | 500 | 2 | 126 |
| $ZnAl_2O_4$ | ZnAl = 1:2, Zn is 50 mM | 130 | 20 | 400 | 4 | 137 |
| $ZnGa_2O_4$ | ZnGa = 1:2, Zn is 50 mM | 130 | 20 | 400 | 4 | 110 |
| $ZnIn_2O_4$ | ZnIn = 1:2, Zn is 50 mM | 130 | 20 | 400 | 4 | 87 |
| $MnCr_2O_4$ | MnCr = 1:2, Mn is 50 mM | 140 | 18 | 450 | 3 | 11 |
| $MnAl_2O_4$ | MnAl = 1:2, y = 2; and Mn is 50 mM | 145 | 16 | 400 | 2 | 15 |
| $MnZr_2O_4$ | MnZr = 1:2, Mn is 50 mM | 150 | 12 | 500 | 1 | 38 |
| $MnIn_2O_4$ | MnIn = 1:2, Mn is 50 mM | 150 | 12 | 500 | 1 | 67 |
| $CoAl_2O_4$ | CoAl = 1:2, Co is 50 mM | 145 | 16 | 400 | 2 | 22 |
| $FeAl_2O_4$ | FeAl = 1:2, Fe is 50 mM | 145 | 16 | 400 | 2 | 30 |
| $InAlMnO_7$ | In:Al:Mn = 1:3:1; Mn is 50 mM | 150 | 12 | 500 | 1 | 84 |
| $InGaMnO_7$ | In:Ga:Mn = 1:2:1; Mn is 50 mM | 145 | 16 | 400 | 2 | 67 |

(VIII) Metal Oxide Dispersed in Dispersant $Cr_2O_3$, $Al_2O_3$ or $ZrO_2$ $Cr_2O_3$, $Al_2O_3$ or $ZrO_2$ dispersed metal oxide was prepared through a precipitate deposition method by taking $Cr_2O_3$, $Al_2O_3$ or $ZrO_2$ as a carrier. By taking preparation of dispersed ZnO as an example, commercial $Cr_2O_3$ (the specific surface area is about 5 $m^2/g$), $Al_2O_3$ (the specific surface area is about 20 $m^2/g$) or $ZrO_2$ (the specific surface area is about 10 $m^2/g$) as a carrier was dispersed in water in advance, and then mixed and precipitated at room temperature with a sodium hydroxide precipitant by taking zinc nitrate as raw material. The molar concentration of $Zn^{2+}$ is 0.067M; and the ratio of molar fractions of $Zn^{2+}$ and the precipitant is 1:8; and then aging was conducted at 160° C. for 24 hours to obtain dispersed ZnO by taking $Cr_2O_3$, $Al_2O_3$ or $ZrO_2$ as the carrier (the contents of the dispersants in the component I are 0.1 wt %, 20 wt % and 85 wt %). The obtained sample was roasted at 500° C. for 1 hour in air. The products were successively defined as dispersed oxides 1-3, and the specific surface areas are successively 148 $m^2/g$, 115 $m^2/g$ and 127 $m^2/g$.

The same method is used to obtain dispersed MnO oxide by taking $SiO_2$ (the specific surface area is about 2 $m^2/g$), $Ga_2O_3$ (the specific surface area is about 10 $m^2/g$), or $TiO_2$ (the specific surface area is about 15 $m^2/g$) as the carrier (the contents of the dispersing agents in the component I are 5 wt %, 30 wt % and 60 wt %). The products are successively defined as dispersed oxides 4-6. The specific surface areas are successively 97 $m^2/g$, 64 $m^2/g$ and 56 $m^2/g$.

The same method is used to obtain dispersed ZnO oxide by taking activated carbon (the specific surface area is about 1000 $m^2/g$), graphene (the specific surface area is about 500 $m^2/g$), or carbon nanotube (the specific surface area is about 300 $m^2/g$) as the carrier (the contents of the dispersing agents in the component I are 5 wt %, 30 wt % and 60 wt %). The products are successively defined as dispersed oxides 7-9. The specific surface areas are successively 177 $m^2/g$, 245 $m^2/g$ and 307 $m^2/g$.

II. Preparation of Component II

The CHA and AEI topology has eight-membered ring orifices and a three-dimensional porous channel.

(I) Zeolite Prepared by Hydrothermal Synthesis

The specific preparation process is as follows:

Component II: taking MgAPO as an example, the raw materials of magnesium nitrate, aluminum hydroxide, phosphoric acid, diisopropylethylamine (DIPEA) and deionized water were weighed according to oxide MgO: $Al_2O_3$:$P_2O_5$: R:$H_2O$=0.3:0.9:1:1.8:45 (molar ratio); the mixture was stirred and aged at 30° C., then transferred into a hydrothermal reactor after 2 h, and crystallized at 180° C. for 120 h. The mixture was cooled to room temperature. Centrifugal washing was conducted repeatedly so that the pH of the supernatant was 7 at the end of washing. After the precipitate was dried at 110° C. for 17 h, the precipitate was roasted in air at 600° C. for 3 h to obtain Mg-doped atomic zeolite.

TABLE 3

Preparation of Heteroatom-Doped Zeolite of CHA or AEI Topology and Performance Parameters

| Zeolite Sample Number | Aluminum Source | P Source | Template Agent R | Heteroatom Reagent M | Molar Ratio ($M:Al_2O_3:P_2O_5:R:H_2O$) | Hydrothermal Temperature/ °C | Time/ day |
|---|---|---|---|---|---|---|---|
| MgAPO | aluminum hydroxide | phosphoric acid | DIPEA | magnesium nitrate | 0.3:0.9:1:1.8:45 | 180 | 5 |
| CaAPO | boehmite | phosphoric acid | TEA | calcium nitrate | 0.1:1:1:3:50 | 200 | 4 |
| TiAPO | aluminum isopropoxide | phosphoric acid | DIPEA | titanium sulfate | 0.15:1:1 1.8:45 | 160 | 7 |
| CrAPO | aluminum hydroxide | phosphoric acid | TEA | chromic nitrate | 0.1:0.9:1:3:50 | 160 | 6 |
| MnAPO | aluminum isopropoxide | phosphoric acid | DIPEA | manganese acetate | 0.1:0.9:1:1.8:45 | 160 | 7 |
| FeAPO | boehmite | phosphoric acid | DIPEA | ferric nitrate | 0.002:1:1:1.8:45 | 200 | 4 |
| CoAPO | aluminum isopropoxide | phosphoric acid | DIPEA | cobalt nitrate | 0.1:0.9:1:1.6:45 | 160 | 7 |
| NiAPO | boehmite | phosphoric acid | TEA | nickel nitrate | 0.2:0.9:1:3:50 | 180 | 4 |
| CuAPO | boehmite | phosphoric acid | DIPEA | copper chloride | 0.005:1:1:1.8:45 | 160 | 6 |
| ZnAPO | aluminum isopropoxide | phosphoric acid | DIPEA | zinc acetate | 0.1:1:1:1.8:45 | 200 | 5 |
| GaAPO | aluminum isopropoxide | phosphoric acid | DIPEA | gallium nitrate | 0.1:0.9:1:1.8:45 | 160 | 5 |
| GeAPO | aluminum isopropoxide | phosphoric acid | DIPEA | germanium oxide | 0.05:0.9:1:1.6:45 | 160 | 7 |
| MoAPO | boehmite | phosphoric acid | DIPEA | ammonium molybdate | 0.2:0.9:1:3:50 | 180 | 5 |
| CdAPO | aluminum hydroxide | phosphoric acid | DIPEA | cadmium nitrate | 0.1:0.9:1:1.8:45 | 180 | 7 |
| SrAPO | aluminum nitrate | phosphoric acid | TEA | strontium nitrate | 0.01:1:1:3:50 | 160 | 6 |

Component II': taking MgSAPO as an example, the raw materials of silica sol, magnesium nitrate, aluminum hydroxide, phosphoric acid, diisopropylethylamine (DIPEA) and deionized water were weighed according to oxide $SiO_2:MgO:Al_2O_3:P_2O_5:R:H_2O=0.1:0.3:0.9:1:1.8:45$ (molar ratio); and other conditions are the same as the preparation of the component II.

TABLE 4

Preparation of Heteroatom-Doped Zeolite of AEI Topology and Performance Parameters

| Zeolite Sample Number | Si Source | Aluminum Source | P Source | Template Agent R | Heteroatom Reagent M | Molar Ratio ($M:Al_2O_3:P_2O_5:R:H_2O$) | Hydrothermal Temperature/ °C | Time/ day |
|---|---|---|---|---|---|---|---|---|
| MgSAPO | silica sol; Si/P = 0.2 | aluminum hydroxide | phosphoric acid | DIPEA | magnesium nitrate | 0.3:0.9:1:1.8:45 | 180 | 5 |
| CaSAPO | | boehmite | phosphoric acid | TEA | calcium nitrate | 0.1:1:1:3:50 | 200 | 4 |
| TiSAPO | | aluminum isopropoxide | phosphoric acid | DIPEA | titanium sulfate | 0.15:1:1:1.8:45 | 160 | 7 |
| CrSAPO | | aluminum hydroxide | phosphoric acid | TEA | chromic nitrate | 0.1:0.9:1:3:50 | 160 | 6 |
| MnSAPO | white carbon | aluminum isopropoxide | phosphoric acid | DIPEA | manganese acetate | 0.1:0.9:1:1.8:45 | 160 | 7 |
| FeSAPO | black; Si/P = 0.01 | boehmite | phosphoric acid | DIPEA | ferric nitrate | 0.002:1:1:1.8:45 | 200 | 4 |
| CoSAPO | | aluminum isopropoxide | phosphoric acid | DIPEA | cobalt nitrate | 0.1:0.9:1:1.6:45 | 160 | 7 |
| NiSAPO | | boehmite | phosphoric acid | TEA | nickel nitrate | 0.2:0.9:1:3:50 | 180 | 4 |
| CuSAPO | silica sol; Si/P = 0.1 | boehmite | phosphoric acid | DIPEA | copper chloride | 0.005:1:1:1.8:45 | 160 | 6 |
| ZnSAPO | | aluminum isopropoxide | phosphoric acid | DIPEA | zinc acetate | 0.1:1:1:1.8:45 | 200 | 5 |
| GaSAPO | | aluminum isopropoxide | phosphoric acid | DIPEA | gallium nitrate | 0.1:0.9:1:1.8:45 | 160 | 5 |

TABLE 4-continued

Preparation of Heteroatom-Doped Zeolite of AEI Topology and Performance Parameters

| Zeolite Sample Number | Si Source | Aluminum Source | P Source | Template Agent R | Heteroatom Reagent M | Molar Ratio $(M:Al_2O_3:P_2O_5:R:H_2O)$ | Hydrothermal Temperature/ ° C. | Time/ day |
|---|---|---|---|---|---|---|---|---|
| GeSAPO | | aluminum isopropoxide | phosphoric acid | DIPEA | germanium oxide | 0.05:0.9:1:1.6:45 | 160 | 7 |
| MoSAPO | white carbon | boehmite | phosphoric acid | DIPEA | ammonium molybdate | 0.2:0.9:1:3:50 | 180 | 5 |
| CdSAPO | black; Si/P = 0.6 | aluminum hydroxide | phosphoric acid | DIPEA | cadmium nitrate | 0.1:0.9:1:1.8:45 | 180 | 7 |
| SrSAPO | | aluminum nitrate | phosphoric acid | TEA | strontium nitrate | 0.01:1:1:3:50 | 160 | 6 |

(II) Zr—AlPO, Ba—Al PO and Ce—Al PO Zeolites Synthesized by Impregnation Method

Component II: 100 mL beaker was taken; a zirconium nitrate solution with appropriate concentration was added into the beaker; the solution was stirred and an appropriate amount of AlPO-18 zeolite was added; the solution was stirred at room temperature until the solution was dry; and the solution was dried and roasted at 600° C. for 3 h to obtain Zr—Al PO. Ba—AlPO and Ce—AlPO zeolites were prepared by the above method; and the precursor was replaced with barium nitrate and cerium nitrate.

Component II': 100 mL beaker was taken; a zirconium nitrate solution with appropriate concentration was added into the beaker; the solution was stirred and an appropriate amount of SAPO-18 zeolite was added; the solution was stirred at room temperature until the solution was dry; and the solution was dried and roasted at 600° C. for 3 h to obtain Zr-SAPO. Ba-SAPO and Ce-SAPO zeolites were prepared by the above method; and the metal source was replaced with barium nitrate and cerium nitrate.

III. Catalyst Preparation

The component I and the component II/II' in the required ratio were added to the container to achieve the purposes of separation, crushing, uniform mixing and the like through one or more than one of extrusion force, impact force, shear force and friction force generated by high-speed motion of the material and/or the container, so as to realize conversion of mechanical energy, thermal energy and chemical energy by regulating the temperature and the atmosphere of carrier gas, thereby further regulating the interaction between different components.

In the mechanical mixing process, the mixing temperature can be set as 20-100° C., and the mechanical mixing process can be conducted in an atmosphere or directly in the air. The atmosphere is selected from any of the following gas:

a) nitrogen and/or inert gas;
b) mixed gas of hydrogen, nitrogen and/or inert gas, with the volume of hydrogen in the mixed gas being 5-50%;
c) mixed gas of CO, nitrogen and/or inert gas, with the volume of CO in the mixed gas being 5-20%;
d) mixed gas of 02, nitrogen and/or inert gas, with the volume of 02 in the mixed gas being 5-20%, wherein the inert gas is one or more than one of helium, argon and neon.

The mechanical mixing can adopt one or more than one of mechanical agitation, ball milling, rocking bed mixing and mechanical grinding for composition. Specifically:

Mechanical stirring: mixing the component I and the component II/II' with a stirring rod in a stirring tank; and regulating the mixing degree of the component I and the component by controlling stirring time (5 min-120 min) and rate (30-300 r/min).

Ball milling: rolling at high speed in a grinding tank by using abrasive and the catalysts; and producing strong impact and milling on the catalysts to achieve the effects of dispersing and mixing the component I and the component II/II'. The ratio of the abrasive (which is stainless steel, agate and quartz; and the size range is 5 mm-15 mm) to the catalysts (the mass ratio range is 20-100:1) is controlled.

Shaking table mixing: premixing the component I and the component II/II' and placing the components into the container; realizing the mixing of the component I and the component by controlling the reciprocating oscillation or circumferential oscillation of a shaking table; and realizing uniform mixing by regulating oscillation speed (range: 1-70 r/min) and time (range: 5 min-120 min).

Mechanical grinding: premixing the component I and the component and placing the components into the container; and under certain pressure (range: 5 kg-20 kg), making relative motion (speed range: 30-300 r/min) by an abrader and mixed catalysts to achieve the effect of uniform mixing.

Specific catalyst preparation and parameter features are shown in Table 5 (component I and component II) and Table 6 (component I and component II').

TABLE 5

Preparation of Catalysts (Component I and Component II) and Parameter Features

| Catalyst Number | Component I | Component II | Weight ratio of Component I to Component II | Compounding Mode and Condition | | | |
|---|---|---|---|---|---|---|---|
| | | | | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| A | ZnO#1 | MgAPO | 0.33 | 5, 30 | | | |
| B | ZnO#2 | CaAPO | 0.5 | 100, 250 | | | |
| C | ZnO#3 | TiAPO | 2 | | 5 mm stainless steel ball, 50:1 | | |
| D | MnO | CrAPO | 1 | | 6 mm stainless steel ball, 60:1 | | |
| E | $CeO_2$ | MnAPO | 1 | | | 5, 10 | |
| F | $Bi_2O_3$ | FeAPO | 3 | | | 60, 100 | |
| G | $In_2O_3$ | CoAPO | 3 | | | | 5, 30 |
| H | $Ga_2O_3$ | NiAPO | 1 | 100, 300 | | | |
| I | $ZnCr_2O_4$ | CuAPO | 5 | | 6 mm agate ball, 100:1 | | |
| J | $ZnAl_2O_4$ | ZnAPO | 1 | | | 70, 100 | |
| K | $ZnGa_2O_4$ | GaAPO | 3 | | | | 15, 200 |
| L | $ZnIn_2O_4$ | GeAPO | 0.33 | | | | 20, 300 |
| M | $MnCr_2O_4$ | MoAPO | 1 | 100, 300 | | | |
| N | $MnAl_2O_4$ | CdAPO | 3 | | 6 mm quartz, 100:1 | | |
| O | $MnZr_2O_4$ | SrAPO | 0.33 | | 6 mm quartz, 100:1 | | |
| P | $MnIn_2O_4$ | Zr—AlPO | 1 | | | | 10, 100 |
| Q | CoAl2O4 | Ba—AlPO | 1 | 100, 250 | | | |
| R | $FeAl_2O_4$ | Ce—AlPO | 3 | | 5 mm stainless steel ball, 50:1 | | |
| S | $InAlMnO_7$ | MgAPO | 1 | | | | 10, 100 |
| T | $InGaMnO_7$ | CaAPO | 4 | | | 50, 60 | |
| U | dispersed oxide 1 | TiAPO | 3 | | | | 10, 100 |
| V | dispersed oxide 2 | CrAPO | 20 | | 5 mm stainless steel ball, 100:1 | | |
| W | dispersed oxide 3 | MnAPO | 0.5 | 5, 30 | | | |
| X | dispersed oxide 4 | FeAPO | 1 | 100, 250 | | | |
| Y | dispersed oxide 5 | CoAPO | 3 | | 5 mm stainless steel ball, 50:1 | | |
| Z | dispersed oxide 6 | NiAPO | 1.5 | | 6 mm stainless steel ball, 60:1 | | |
| Z1 | dispersed oxide 7 | CuAPO | 2.5 | | | 5, 10 | |
| Z2 | dispersed oxide 8 | ZnAPO | 1.5 | | | 60, 100 | |
| Z3 | dispersed oxide 9 | GaAPO | 2 | | | | 5, 30 |
| Reference example 1 | ZnO#4 | GeAPO | 3 | | | 20, 30 | |

TABLE 5-continued

Preparation of Catalysts (Component I and Component II) and Parameter Features

| | | | | Compounding Mode and Condition | | | |
|---|---|---|---|---|---|---|---|
| Catalyst Number | Component I | Component II | Weight ratio of Component I to Component II | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| Reference example 2 | composite metal ZnCo, the molar ratio of Zn to Co is 1:1. | MoAPO | 2 | | 5 mm stainless steel ball, 50:1 | | |
| Reference example 3 | $TiO_2$ | CdAPO | 2 | | 5 mm stainless steel ball, 50:1 | | |

TABLE 6

Preparation of Catalysts (Component I and Component II') and Parameter Features

| | | | | Compounding Mode and Condition | | | |
|---|---|---|---|---|---|---|---|
| Catalyst Number | Component I | Component II' | Weight ratio of Component I to Component II' | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| A' | ZnO#1 | MgSAPO | 0.33 | 5, 30 | | | |
| B' | ZnO#2 | CaSAPO | 0.5 | 100, 250 | | | |
| C' | ZnO#3 | TiSAPO | 2 | | 5 mm stainless steel ball, 50:1 | | |
| D' | MnO | CrSAPO | 1 | | 6 mm stainless steel ball, 60:1 | | |
| E' | $CeO_2$ | MnSAPO | 1 | | | 5, 10 | |
| F' | $Bi_2O_3$ | FeSAPO | 3 | | | 60, 100 | |
| G' | $In_2O_3$ | CoSAPO | 3 | | | | 5, 30 |
| H' | $Ga_2O_3$ | NiSAPO | 1 | 100, 300 | | | |
| I' | $ZnCr_2O_4$ | CuSAPO | 5 | | 6 mm agate ball, 100:1 | | |
| J' | $ZnAl_2O_4$ | ZnSAPO | 1 | | | 70, 100 | |
| K' | $ZnGa_2O_4$ | GaSAPO | 3 | | | | 15, 200 |
| L' | $ZnIn_2O_4$ | GeSAPO | 0.33 | | | | 20, 300 |
| M' | $MnCr_2O_4$ | MoSAPO | 1 | 100, 300 | | | |
| N' | $MnAl_2O_4$ | CdSAPO | 3 | | 6 mm quartz, 100:1 | | |
| O' | $MnZr_2O_4$ | SrSAPO | 0.33 | | 6 mm quartz, 100:1 | | |
| P' | $MnIn_2O_4$ | Zr—SAPO | 1 | | | | 10, 100 |
| Q' | $CoAl2O4$ | Ba—SAPO | 1 | 100, 250 | | | |
| R' | $FeAl_2O_4$ | Ce—SAPO | 3 | | 5 mm stainless steel ball, 50:1 | | |

TABLE 6-continued

Preparation of Catalysts (Component I and Component II') and Parameter Features

| | | | | Compounding Mode and Condition | | | |
|---|---|---|---|---|---|---|---|
| Catalyst Number | Component I | Component II' | Weight ratio of Component I to Component II' | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) |
| S' | InAlMnO$_7$ | MgSAPO | 1 | | | | 10, 100 |
| T' | InGaMnO$_7$ | CaSAPO | 4 | | | 50, 60 | |
| U' | dispersed oxide 1 | TiSAPO | 3 | | | | 10, 100 |
| V' | dispersed oxide 2 | CrSAPO | 20 | | 5 mm stainless steel ball, 100:1 | | |
| W' | dispersed oxide 3 | MnSAPO | 0.5 | 5, 30 | | | |
| X' | dispersed oxide 4 | FeSAPO | 1 | 100, 250 | | | |
| Y' | dispersed oxide 5 | CoSAPO | 3 | | 5 mm stainless steel ball, 50:1 | | |
| Z' | dispersed oxide 6 | NiSAPO | 1.5 | | 6 mm stainless steel ball, 60:1 | | |
| Z1' | dispersed oxide 7 | CuSAPO | 2.5 | | | 5, 10 | |
| Z2' | dispersed oxide 8 | ZnSAPO | 1.5 | | | 60, 100 | |
| Z3' | dispersed oxide 9 | GaSAPO | 2 | | | | 5, 30 |
| Reference example 1' | ZnO#4 | GeSAPO | 3 | | | 20, 30 | |
| Reference example 2' | composite metal ZnCo, the molar ratio of Zn to Co is 1:1. | MoSAPO | 2 | | 5 mm stainless steel ball, 50:1 | | |
| Reference example 3' | TiO$_2$ | CdSAPO | 2 | | 5 mm stainless steel ball, 50:1 | | |

Example of Catalytic Reactions

A fixed bed reaction is taken as an example, but the catalyst is also applicable to a fluidized bed reactor. The apparatus is equipped with gas mass flow meters and online product analysis chromatography (the tail gas of the reactor is directly connected with the metering valve of chromatography, and thus periodic and real-time sampling and analysis will be achieved).

2 g of the above catalyst in the present invention was placed in a fixed bed reactor. The air in the reactor was replaced with Ar; and then the temperature was raised to 300° C. in the H$_2$ atmosphere, and then the syngas (H$_2$/CO molar ratio=0.2-3.5) was switched. The pressure of the syngas was 0.5-10 MPa. The temperature was raised to reaction temperature of 300-600° C., and the air velocity of the reaction raw gas was regulated to 300-12000 ml/g/h. On-line chromatography was used to detect and analyze the product.

The reaction performance can be changed by changing the temperature, pressure, space velocity and H$_2$/CO molar ratio in the syngas. The sum of propylene and butylene selectivity is 30-75%. The sum of selectivity of the light olefin, the ethylene, the propylene and the butylene is 50-90%. Due to the low hydrogenation activity of the surface of the metal composite of the catalyst, a large amount of methane will not be generated and the selectivity of the methane is low. Table 7 (component I and component II) and Table 8 (component I and component II') list specific application and effect data of the catalysts respectively.

TABLE 7

Specific Application and Effect Data of Catalysts (Component I and Component II)

| Embodiments | Catalysts | GHSV($h^{-1}$) | Temperature (° C.) | $H_2$/CO Molar Ratio | Pressure (MPa) | CO Conversion Rate % | Light Olefin Selectivity % | $CH_4$ Selectivity % | Propylene and Butylene Selectivities % |
|---|---|---|---|---|---|---|---|---|---|
| 1 | A | 5000 | 415 | 2.5 | 4 | 41.6 | 71.8 | 5.7 | 58.2 |
| 2 | B | 4000 | 410 | 1.5 | 6 | 31.5 | 62.7 | 5.4 | 42.0 |
| 3 | C | 5000 | 400 | 2.5 | 4 | 11.3 | 61.1 | 6.9 | 36.7 |
| 4 | D | 7000 | 420 | 1 | 10 | 37.1 | 65.3 | 6.1 | 54.3 |
| 5 | E | 2000 | 390 | 3.5 | 6 | 20.2 | 80.7 | 4.7 | 67.3 |
| 6 | F | 2000 | 410 | 1.5 | 3 | 31.3 | 64.4 | 5.5 | 47.7 |
| 7 | G | 3500 | 390 | 3.5 | 2.5 | 35.1 | 73.2 | 5.4 | 62.2 |
| 8 | H | 1500 | 370 | 2.5 | 5 | 19.6 | 82.1 | 4.5 | 64.7 |
| 9 | I | 2500 | 400 | 3 | 3.5 | 42.0 | 71.0 | 2.2 | 56.5 |
| 10 | J | 2000 | 410 | 2.5 | 8 | 55.2 | 73.6 | 3.4 | 62.7 |
| 11 | K | 1000 | 410 | 2.5 | 6 | 20.2 | 69.1 | 6.8 | 50.1 |
| 12 | L | 5000 | 400 | 2.5 | 4 | 33.0 | 85.1 | 2.6 | 63.1 |
| 13 | M | 10500 | 520 | 0.5 | 1 | 15.4 | 72.0 | 7.6 | 57.6 |
| 14 | N | 3000 | 480 | 0.5 | 2 | 31.7 | 73.4 | 6.2 | 60.7 |
| 15 | O | 3000 | 470 | 0.5 | 2 | 25.4 | 76.0 | 5.4 | 60.8 |
| 16 | P | 3000 | 450 | 1 | 3 | 30.8 | 61.9 | 6.2 | 40.2 |
| 17 | Q | 3000 | 450 | 1.5 | 3 | 33.5 | 65.7 | 6.8 | 43.5 |
| 18 | R | 3000 | 350 | 3.5 | 5 | 33.0 | 52.2 | 5.6 | 40.7 |
| 19 | S | 2000 | 350 | 3 | 7 | 38.6 | 55.3 | 6.9 | 40.9 |
| 20 | T | 2500 | 400 | 1 | 6 | 19.0 | 63.8 | 5.7 | 45.7 |
| 21 | U | 4000 | 400 | 2 | 4 | 10.1 | 64.2 | 6.5 | 41.4 |
| 22 | V | 8000 | 450 | 0.5 | 2 | 21.1 | 53.0 | 6.3 | 42.6 |
| 23 | W | 2000 | 410 | 2 | 3.5 | 30.8 | 78.3 | 4.9 | 62.8 |
| 24 | X | 3000 | 380 | 3.5 | 6 | 31.6 | 74.4 | 7.0 | 56.0 |
| 25 | Y | 5000 | 390 | 3 | 2.5 | 25.7 | 69.9 | 2.5 | 59.8 |
| 26 | Z | 4000 | 370 | 2 | 10 | 28.2 | 83.7 | 6.7 | 70.3 |
| 27 | Z 1 | 10000 | 470 | 1 | 1.5 | 17.7 | 71.1 | 6.8 | 57.5 |
| 28 | Z 2 | 2000 | 400 | 3.5 | 7 | 46.8 | 78.6 | 4.3 | 65.7 |
| 29 | Z 3 | 3000 | 380 | 1.5 | 2.5 | 11.3 | 55.3 | 6.2 | 35.1 |
| 38 | Reference example 1 | 3000 | 320 | 0.5 | 1 | 1.1 | 26.0 | 37.2 | 11.1 |
| 39 | Reference example 2 | 4000 | 450 | 3 | 3 | 24.4 | 33.4 | 25.3 | 13.2 |
| 40 | Reference example 3 | 2000 | 350 | 2.5 | 3 | 0.1 | 18.4 | 67.2 | 6.6 |
| 41 | Reference example 4 | 2000 | 410 | 1.5 | 3 | 24.6 | 46.2 | 9.7 | 25.6 |
| 42 | Reference example 5 | 3000 | 400 | 2 | 3.5 | 31.2 | 19.5 | 10.8 | 12.7 |
| 43 | Reference example 6 | 3000 | 450 | 2.5 | 4 | 8.3 | 1.5 | 50 | 0.7 |
| 44 | Reference example 7 | 2200 | 450 | 3 | 2 | <1 | — | — | — |
| 45 | Reference example 8 | 5000 | 415 | 2.5 | 4 | 8.4 | 59.0 | 20.6 | 40.2 |
| 46 | Reference example 9 | 5000 | 415 | 2.5 | 4 | 9.4 | 55.4 | 22.6 | 37.1 |
| 47 | Reference example 10 | 4000 | 410 | 1.5 | 6 | 17.3 | 57.7 | 21.4 | 38.3 |

In reference example 1, the catalyst component I is ZnO #4, and component II is GeAPO.

The zeolite in the catalyst adopted in reference example 4 is a commodity SAPO-34 purchased from Nankai University Catalyst Factory, wherein the temperature of desorption peak of mediate strong acid on NH3-TPD is 390° C. and the amount of the mediate strong acid sites is 0.6 mol/kg.

The zeolite in the catalyst adopted in reference example 5 is a commodity ZSM-5 purchased from Nankai University Catalyst Factory, wherein the zeolite is of a full microporous structure, and the silica alumina ratio is 30.

Reaction results of reference examples 4 and 5 show that, the topology and acid strength of CHA or AEI are crucial to the selective modulation of the products.

The catalyst adopted in reference example 6 is a sample containing only component IZnO #1 without the zeolite, and the reaction conversion rate is very low. The products mainly comprise by-products such as dimethyl ether and methane, and almost no ethylene is produced.

The catalyst adopted in reference example 7 is a sample containing only component II and part 1 zeolite without the component I, and the catalytic reaction almost has no activity.

Reference examples 6 and 7 have extremely poor reaction effects when only containing component I or component II on the surface, and do not have the excellent reaction performance described in the present invention.

The zeolite in the catalyst adopted in reference example 8 is self-synthetic AlPO-18. Other parameters and the mixing process are the same as those of catalyst A. The conversion rate and selectivity of the reaction in the reference example 8 are very poor, which are far lower than the reaction performance of catalyst A under the same conditions. This indicates that the zeolite doped with the heteroatoms can effectively improve the reaction activity and selectivity.

The zeolite in the catalyst adopted in reference example 9 is AlPO-18 after $Mg(NO_3)_2$ ion exchange. Other parameters and the mixing process are the same as those of catalyst A.

The zeolite in the catalyst adopted in reference example 10 is AlPO-34 after $Ca(NO_3)_2$ ion exchange. Other parameters and the mixing process are the same as those of catalyst B.

The reaction results of reference example 9 and reference example 10 show that the reaction performance of ion-exchanged AlPO-18 and AlPO-34 samples as catalyst component II has obvious gap from the heteroatom-doped zeolite of the present invention; and the doping of the heteroatoms in the AlPO zeolite skeleton is very important for the reaction activity and selective modulation.

TABLE 8

Specific Application and Effect Data of Catalysts (Component I and Component II')

| Embodiments | Catalysts | GHSV($h^{-1}$) | Temperature (° C.) | $H_2$/CO Molar Ratio | Pressure (MPa) | CO Conversion Rate % | Light Olefin Selectivity % | $CH_4$ Selectivity % | Propylene and Butylene Selectivities % |
|---|---|---|---|---|---|---|---|---|---|
| 1 | A' | 5000 | 400 | 2.5 | 5 | 38.7 | 78.6 | 4.7 | 62.2 |
| 2 | B' | 4000 | 410 | 1.5 | 9 | 30.5 | 60.2 | 6.4 | 44.0 |
| 3 | C' | 5000 | 400 | 2.5 | 4 | 21.3 | 65.1 | 6.8 | 50.7 |
| 4 | D' | 7000 | 420 | 1 | 10 | 51.1 | 66.4 | 6.1 | 54.8 |
| 5 | E' | 2000 | 390 | 3.5 | 6 | 27.3 | 81.5 | 4.7 | 72.4 |
| 6 | F' | 2000 | 410 | 1.5 | 3 | 34.1 | 61.1 | 5.5 | 49.8 |
| 7 | G' | 3500 | 390 | 3.5 | 2.5 | 38.2 | 71.3 | 5.4 | 60.7 |
| 8 | H' | 1500 | 370 | 2.5 | 5 | 24.6 | 75.4 | 6.5 | 60.1 |
| 9 | I' | 2500 | 400 | 3 | 3.5 | 45.2 | 69.3 | 4.2 | 56.0 |
| 10 | J' | 2000 | 410 | 2.5 | 8 | 57.5 | 73.1 | 6.4 | 61.4 |
| 11 | K' | 1000 | 410 | 2.5 | 6 | 30.7 | 65.2 | 6.8 | 50.6 |
| 12 | L' | 5000 | 400 | 2.5 | 4 | 42.1 | 76.3 | 3.6 | 64.5 |
| 13 | M' | 10500 | 520 | 0.5 | 1 | 15.4 | 51.1 | 2.6 | 43.5 |
| 14 | N' | 3000 | 480 | 0.5 | 2 | 34.6 | 63.4 | 4.2 | 50.2 |
| 15 | O' | 3000 | 470 | 0.5 | 2 | 32.4 | 66.0 | 4.8 | 56.7 |
| 16 | P' | 3000 | 450 | 1 | 3 | 30.8 | 65.4 | 5.2 | 52.2 |
| 17 | Q' | 3000 | 450 | 1.5 | 3 | 38.5 | 61.2 | 6.8 | 48.3 |
| 18 | R' | 3000 | 350 | 3.5 | 5 | 37.3 | 50.1 | 5.6 | 39.7 |
| 19 | S' | 2000 | 350 | 3 | 7 | 41.6 | 51.3 | 5.9 | 40.9 |
| 20 | T' | 2500 | 400 | 1 | 6 | 28.1 | 69.8 | 5.7 | 45.7 |
| 21 | U' | 4000 | 400 | 2 | 4 | 30.1 | 66.2 | 6.5 | 54.4 |
| 22 | V' | 8000 | 450 | 0.5 | 2 | 18.1 | 63.0 | 3.3 | 52.1 |
| 23 | W' | 2000 | 410 | 2 | 3.5 | 32.8 | 75.3 | 4.9 | 64.4 |
| 24 | X' | 3000 | 380 | 3.5 | 6 | 38.6 | 72.4 | 5.1 | 54.2 |
| 25 | Y' | 5000 | 390 | 3 | 2.5 | 28.1 | 65.4 | 3.5 | 57.2 |
| 26 | Z' | 4000 | 370 | 2 | 10 | 31.2 | 71.7 | 6.1 | 55.3 |
| 27 | Z 1' | 10000 | 470 | 1 | 1.5 | 21.7 | 69.8 | 3.8 | 51.7 |
| 28 | Z 2' | 2000 | 400 | 3.5 | 7 | 51.8 | 72.3 | 6.1 | 60.8 |
| 29 | Z 3' | 3000 | 380 | 1.5 | 2.5 | 21.3 | 57.3 | 6.2 | 39.8 |
| 38 | Reference example 1' | 3000 | 320 | 0.5 | 1 | 1.3 | 28.5 | 32.1 | 16.6 |
| 39 | Reference example 2' | 4000 | 450 | 3 | 3 | 27.5 | 30.2 | 21.4 | 15.7 |
| 40 | Reference example 3' | 2000 | 350 | 2.5 | 3 | 0.2 | 18.3 | 64.4 | 9.8 |
| 41 | Reference example 4' | 2000 | 410 | 1.5 | 3 | 24.6 | 46.2 | 9.7 | 25.6 |
| 42 | Reference example 5' | 3000 | 400 | 2 | 3.5 | 31.2 | 19.5 | 10.8 | 12.7 |
| 43 | Reference example 6' | 3000 | 450 | 2.5 | 4 | 8.3 | 1.5 | 50 | 0.7 |
| 44 | Reference example 7' | 2200 | 450 | 3 | 2 | <1 | — | — | — |
| 45 | Reference example 8' | 5000 | 400 | 2.5 | 5 | 40.6 | 68.8 | 5.7 | 54.2 |

TABLE 8-continued

Specific Application and Effect Data of Catalysts (Component I and Component II')

| Embodiments | Catalysts | GHSV($h^{-1}$) | Temperature (° C.) | $H_2$/CO Molar Ratio | Pressure (MPa) | CO Conversion Rate % | Light Olefin Selectivity % | $CH_4$ Selectivity % | Propylene and Butylene Selectivities % |
|---|---|---|---|---|---|---|---|---|---|
| 46 | Reference example 9' | 4000 | 410 | 1.5 | 9 | 30.5 | 52.2 | 10.2 | 34.0 |
| 47 | Reference example 10' | 5000 | 400 | 2.5 | 4 | 21.3 | 55.1 | 15.8 | 35.7 |

In reference example 1', the catalyst component I is ZnO #4, and component II' is GeSAPO.

The zeolite in the catalyst adopted in reference example 4' is a commodity SAPO-34 purchased from Nankai University Catalyst Factory, wherein the temperature of desorption peak of mediate strong acid on NH3-TPD is 390° C. and the amount of the mediate strong acid sites is 0.6 mol/kg.

The zeolite in the catalyst adopted in reference example 5' is a commodity ZSM-5 purchased from Nankai University Catalyst Factory, wherein the zeolite is of a full microporous structure, and the silica alumina ratio is 30.

Reaction results of reference examples 4' and 5' show that, the topology and acid strength of CHA or AEI are crucial to the selective modulation of the products.

The catalyst adopted in reference example 6' is a sample containing only component IZnO #1 without the zeolite, and the reaction conversion rate is very low. The products mainly comprise by-products such as dimethyl ether and methane, and almost no ethylene is produced.

The catalyst adopted in reference example 7' is a sample containing only component II' and part 1 zeolite without the component I, and the catalytic reaction almost has no activity.

Reference examples 6' and 7' have extremely poor reaction effects when only containing component I or component II' on the surface, and do not have the excellent reaction performance described in the present invention.

The zeolite in the catalyst adopted in reference example 8' is self-synthetic SAPO-18. Other parameters and the mixing process are the same as those of catalyst A'. Catalyst A doped with Mg on the basis of the reaction of reference example 8 having higher conversion rate and poor selectivity can effectively improve the selectivity for light olefin.

The zeolite in the catalyst adopted in reference example 9' is SAPO-18, after Mg($NO_3$)$_2$ ion exchange. Other parameters and the mixing process are the same as those of catalyst A'.

The zeolite in the catalyst adopted in reference example 10' is SAPO-34 after Ca($NO_3$)$_2$ ion exchange. Other parameters and the mixing process are the same as those of catalyst B'.

The reaction results of reference example 9' and reference example 10' show that the reaction performance of ion-exchanged SAPO-18 and SAPO-34 samples as catalyst component II' has obvious gap from the heteroatom-doped zeolite of the present invention; and the conversion rate and the selectivity are obviously reduced. The doping of the heteroatoms in the SAPO zeolite skeleton is very important for the reaction activity and selective modulation.

In the reference technology of the document (Jiao et al., Science 351 (2016) 1065-1068), the acid amount of the used SAPO-34 zeolite is large. The acid amount of the mediate strong acid reaches 0.32 mol/kg according to the NH3-TPD test. Therefore, when the conversion rate is increased to 35%, alkene selectivity is 69%, alkane selectivity is 20%, alkene/alkane ratio is decreased to 3.5 and propylene and butylene selectivity is 40-50%.

It is observed from the above table that, the structure of the zeolite including the topologies, acid strength and acid amount of CHA&AEI, doping amount of heteroatoms and doping in the skeleton, and the matching between the metal oxide and the zeolite are crucial and directly affect the conversion rate of carbon monoxide and propylene and butylene selectivity.

The invention claimed is:

1. A catalyst comprising a component I and a component II, wherein an active ingredient of the component I is a metal oxide, and the component II is a heteroatom-doped zeolite; the metal oxide is at least one of $MnO_x$, $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $CeO_x$, $Co_aAl_{(1-a)}O_x$, $Fe_aAl_{(1-a)}O_x$, $GaO_x$, $BiO_x$, $InO_x$, $In_aAl_bMn_{(1-a-b)}O_x$ and $In_aGa_bMn_{(1-a-b)}O_x$; a value range of x is 0.7-3.7; a value range of a is 0-1; and a value range of a+b is 0-1;
the zeolite is a zeolite with CHA or AEI topology, whose skeleton atoms comprise Al—P—O or Si—Al—P—O; the heteroatom is at least one of divalent metal Mg, Ca, Cr, Mn, Fe, Co, Ni, Cu, Zn, Sr, Zr, Mo, Cd, Ba and Ce, trivalent metal Ti and Ga, and tetravalent metal Ge; the heteroatom-doped zeolite means that the heteroatom is doped in a zeolite skeleton to replace Al, P or Si in the zeolite skeleton.

2. The catalyst according to claim 1, wherein a specific surface area of $MnO_x$, $ZnO_x$, $CeO_x$, $GaO_x$, $BiO_x$, and $InO_x$ is 1-100 $m^2$/g;
a specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$, and $In_aGa_bMn_{(1-a-b)}O_x$ is 5-150 $m^2$/g.

3. The catalyst according to claim 1, wherein a ratio of the sum of the molar weight of the heteroatoms in the heteroatom-doped zeolite to the molar weight of P is 0.001-0.6.

4. The catalyst according to claim 1, wherein a weight ratio of the active ingredient in the component I to the component II is 0.1-20.

5. The catalyst according to claim 1, wherein a dispersant is added to the component I, and the metal oxide is dispersed in the dispersant; the dispersant is at least one of $Al_2O_3$, $SiO_2$, $Cr_2O_3$, $ZrO_2$, $TiO_2$, $Ga_2O_3$, activated carbon, graphene, and carbon nanotube; and in the component I, the content of the dispersant is 0.05-90 wt. %, and the balance is the metal oxide.

6. The catalyst according to claim 1, wherein the heteroatom-doped zeolite is prepared by an in-situ hydrothermal growth method or a post-treatment method; the in-situ hydrothermal growth method comprises the following steps:
(1) preparation of a sol precursor:
Al—P—O skeleton: dissolving a certain proportion of aluminum source and phosphorus source in water and stirring evenly; then adding a heteroatom-containing precursor and a template agent and stirring for 0.5-12 h;
Si—Al—P—O skeleton: dissolving a certain proportion of aluminum source, phosphorus source and silicon source in water and stirring evenly; then adding the heteroatom-containing precursor and the template agent and stirring for 0.5-12 h;
(2) hydrothermal crystallization: crystallizing the sol precursor obtained in step (1) at 160-200° C. for 4-7 days;
(3) separation and washing: centrifuging, washing and drying the product after the crystallization reaction;
(4) drying and roasting: roasting the product of step (3) at 550-600° C. for 3-6 h, wherein a molar ratio of the heteroatoms in the heteroatom precursor to the phosphorus source is 0-0.6;
the post-treatment method comprises:
Al—P—O skeleton: configuring a solution of the heteroatom precursor; impregnating AlPO-18 or AlPO-34 zeolite into the solution of the heteroatom precursor; drying the solution; finally roasting the solution at 550-600° C. for 3-6 h;
Si—Al—P—O skeleton: configuring a solution of the heteroatom precursor; impregnating SAPO-18 or SAPO-34 zeolite into the solution of the heteroatom precursor; drying the solution; and finally roasting the solution at 550-600° C. for 3-6 h.

7. The catalyst according to claim 6, wherein the aluminum source is boehmite, aluminum hydroxide, aluminum nitrate, aluminum sulfate, or aluminum isopropoxide; the phosphorus source is phosphoric acid; the silicon source is silica sol, TEOS, white carbon black, quartz sand, or silicate; the heteroatom precursor is metal nitrate, sulfate, acetate, halide or oxide of a corresponding metal atom; the template agent is triethylamine or diisopropylethylamine.

8. A method for preparing light olefin through catalytic syngas with high selectivity comprising subjecting the syngas to a conversion reaction on a fixed bed or a moving bed to prepare light olefin in the presence of the catalyst of claim 1.

9. The method according to claim 8, wherein the conversion reaction is conducted at a pressure of the syngas of 0.5-10 MPa, a reaction temperature of 300-600° C., a space velocity of 300-10000 $h^{-1}$, and wherein the syngas is a mixed gas of $H_2$/CO with a molar ratio of Hz/CO of 0.2-3.5.

10. The method according to claim 9, wherein $C_{2-4}$ olefin is prepared using one-step direct conversion of syngas; a selectivity for $C_{2-4}$ olefin is 50-90%; and a selectivity for a methane side product is lower than 7%.

11. The catalyst according to claim 1, wherein a specific surface area of $MnO_x$, $ZnO_x$, $CeO_x$, $GaO_x$, $BiO_x$, and $InO_x$ is 50-100 $m^2$/g; and
a specific surface area of $Mn_aCr_{(1-a)}O_x$, $Mn_aAl_{(1-a)}O_x$, $Mn_aZr_{(1-a)}O_x$, $Mn_aIn_{(1-a)}O_x$, $ZnO_x$, $Zn_aCr_{(1-a)}O_x$, $Zn_aAl_{(1-a)}O_x$, $Zn_aGa_{(1-a)}O_x$, $Zn_aIn_{(1-a)}O_x$, $Co_aAl_{(1-a)}O_x$, $Fe_aAl_{(1-a)}O_x$, $In_aAl_bMn_{(1-a-b)}O_x$ and $In_aGa_bMn_{(1-a-b)}O_x$ is 50-150 $m^2$/g.

12. The catalyst according to claim 1, wherein a weight ratio of the active ingredient in the component I to the component II is 0.3-5.

13. The method according to claim 8, wherein the conversion reaction is conducted at a pressure of the syngas of 1-8 MPa, a reaction temperature of 370-450° C., and a space velocity of 500-9000 $h^{-1}$ and wherein the syngas is a mixed gas of $H_2$/CO with a molar ratio of $H_2$/CO of 0.3-2.5.

14. The method according to claim 8, wherein the conversion reaction is conducted at a pressure of the syngas of 2-8 MPa and a space velocity of 1000-6000 $h^{-1}$.

15. The method according to claim 8, wherein the syngas contains $CO_2$, and a volume concentration of $CO_2$ in the syngas is 0.1-50%.

* * * * *